United States Patent
Park et al.

(10) Patent No.: US 11,627,895 B2
(45) Date of Patent: Apr. 18, 2023

(54) APPARATUS AND METHOD FOR ESTIMATING ANALYTE CONCENTRATION, AND APPARATUS AND METHOD FOR GENERATING ANALYTE CONCENTRATION ESTIMATION MODEL

(71) Applicant: SAMSUNG ELECTRONICS CO., LTD., Suwon-si (KR)

(72) Inventors: Yun S Park, Suwon-si (KR); Sung Hyun Nam, Yongin-si (KR); Woo Chang Lee, Anyang-si (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 827 days.

(21) Appl. No.: 16/527,983

(22) Filed: Jul. 31, 2019

(65) Prior Publication Data

US 2020/0046269 A1     Feb. 13, 2020

Related U.S. Application Data

(60) Provisional application No. 62/717,232, filed on Aug. 10, 2018.

(30) Foreign Application Priority Data

Aug. 23, 2018   (KR) .................. 10-2018-0098772

(51) Int. Cl.
*A61B 5/145*     (2006.01)
*A61B 5/1455*    (2006.01)
(Continued)

(52) U.S. Cl.
CPC ........ *A61B 5/14532* (2013.01); *A61B 5/1455* (2013.01); *A61B 5/1477* (2013.01);
(Continued)

(58) Field of Classification Search
CPC ............ A61B 5/14532; A61B 5/14546; A61B 5/1455; A61B 5/1477; A61B 5/681;
(Continued)

(56) References Cited

U.S. PATENT DOCUMENTS 6,181,957 B1    1/2001  Lambert et al.
6,690,966 B1    2/2004  Rava et al.
(Continued)

FOREIGN PATENT DOCUMENTS

EP    0573535 B1 *  12/2000  ........... A61B 5/0071
JP    6-505183 A    6/1994
(Continued)

OTHER PUBLICATIONS

Zanyar Movasaghi et al. "Raman Spectroscopy of Biological Tissues" Applied Spectroscopy Reviews, vol. 42, No. 5, Sep. 1, 2007, (pp. 493-541) XP055333224.

(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

A apparatus for estimating concentration may include: a spectrum obtainer configured to obtain Raman spectra of an object; and a processor configured to extract, from the Raman spectra, at least one analyte spectrum related to an analyte and at least one non-analyte spectrum related to a biological component other than the analyte, and estimate concentration of the analyte based on a first area under a curve of the at least one analyte spectrum and a second area under a curve of the at least one non-analyte spectrum.

20 Claims, 17 Drawing Sheets

(51) Int. Cl.
  *A61B 5/1477* (2006.01)
  *A61B 5/00* (2006.01)
  *G01J 3/44* (2006.01)
  *G01N 21/65* (2006.01)

(52) U.S. Cl.
  CPC .......... *A61B 5/14546* (2013.01); *A61B 5/681* (2013.01); *G01J 3/44* (2013.01); *G01N 21/658* (2013.01)

(58) Field of Classification Search
  CPC ................ A61B 5/7242; A61B 5/4869; A61B 5/6898; G01J 3/44; G01N 21/658
  See application file for complete search history.

(56) References Cited

U.S. PATENT DOCUMENTS

| | | |
|---|---|---|
| 6,697,665 B1 | 2/2004 | Rava et al. |
| 6,868,285 B2 | 3/2005 | Muller-Dethlefs |
| 7,039,446 B2 | 5/2006 | Ruchti et al. |
| 8,027,033 B2 | 9/2011 | Lipson et al. |
| 9,662,047 B2 | 5/2017 | Barman et al. |
| 2004/0186383 A1 | 9/2004 | Rava et al. |
| 2007/0291251 A1 | 12/2007 | Rensen et al. |
| 2014/0349337 A1 | 11/2014 | Dasari et al. |
| 2016/0139045 A1 | 5/2016 | Gulati et al. |
| 2016/0235345 A1* | 8/2016 | Perez Calero ....... A61B 5/0075 |
| 2017/0127983 A1 | 5/2017 | Spegazzini et al. |
| 2017/0135645 A1 | 5/2017 | Shin et al. |
| 2017/0319185 A1 | 11/2017 | Choi et al. |

FOREIGN PATENT DOCUMENTS

| | | |
|---|---|---|
| JP | 2003-534087 A | 11/2003 |
| KR | 10-2017-0057083 A | 5/2017 |
| KR | 10-2017-0126310 A | 11/2017 |
| WO | 0573535 A1 | 9/1992 |
| WO | 2017/083593 A1 | 5/2017 |

OTHER PUBLICATIONS

James P. Wicksted et al. "Raman Spectroscopy Studies of Metabolic Concentrations in Aqueous Solutions and Aqueous Humor Specimens" Applied Spectroscopy, vol. 49, No. 7, Jan. 1, 1995, (pp. 987-993) XP000877061.

Communication dated Nov. 20, 2019, issued by the European Patent Office in counterpart European Application No. 19191000.9.

Sana Tfaili, "Confocal Raman microspectroscopy for skin characterization: a comparative study between human skin and pig skin", Analyst, No. 137, The Royal Society of Chemistry, Jul. 2012, 11 pages.

Stefan Soderholm et al., "Raman Spectra of Fructose and Glucose in the Amorphous and Crystalline States", Journal of Raman Spectroscopy, No. 30, John Wiley & Sons, Ltd., May 18, 1999, pp. 1009-1018.

Roman Rosipal et al., "Overview and Recent Advances in Partial Least Squares", Nov. 2005, pp. 34-51.

Jingwei Shao et al., "In Vivo Blood Glucose Quantification Using Raman Spectroscopy", PLOS One, vol. 7, Issue 10, Oct. 25, 2012, pp. 1-6.

Abraham Savitzky et al., "Smoothing and Differentiation of Data by Simplified Least Squares Procedures", Analytical Chemistry, vol. 36, No. 8, ACS Publications, Jul. 1, 1964, pp. 1627-1639.

Sana Tfaili et al., "Confocal Raman microspectroscopy for skin characterization: a comparative study between human skin and pig skin", Analyst, No. 137, The Royal Society of Chemistry, Jul. 2012, 11 pages.

Roman Rosipal et al., "Overview and Recent Advances in Partial Least Squares", SLSFS 2005, LNCS 3940, Springer, Nov. 2005, pp. 34-51.

Jingwei Shao et al., "In Vivo Blood Glucose Quantification Using Raman Spectroscopy", PLOS One, vol. 7, Issue 10, Oct. 2012, pp. 1-6.

Abraham Savitzky et al., "Smoothing and Differentiation of Data by Simplified Least Squares Procedures", Analytical Chemistry, vol. 36, No. 8, ACS Publications, Jul. 1964, pp. 1627-1639.

Communication dated Jan. 11, 2023, issued by the Korean Intellectual Property Office in Korean Patent Application No. 10-2018-0098772.

* cited by examiner

APPARATUS AND METHOD FOR ESTIMATING ANALYTE CONCENTRATION, AND APPARATUS AND METHOD FOR GENERATING ANALYTE CONCENTRATION ESTIMATION MODEL

CROSS-REFERENCE TO RELATED APPLICATION(S)

This application claims priority from U.S. Application No. 62/717,232, filed on Aug. 10, 2018 in the U.S. Patent and Trademark Office, and Korean Patent Application No. 10-2018-0098772, filed on Aug. 23, 2018 in the Korean Intellectual Property Office, the disclosures of which are incorporated herein by reference in their entireties.

BACKGROUND

1. Field

Apparatuses and methods consistent with example embodiments relate to estimating concentration of an analyte in a non-invasive manner.

2. Description of the Related Art

Diabetes is a chronic disease that causes various complications and can be hardly cured, such that people with diabetes are advised to check their blood glucose regularly to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections due to the use of injection. Recently, research has been conducted on non-invasive methods of measuring blood glucose by using a spectrometer without drawing blood.

SUMMARY

One or more example embodiments provide an apparatus and method for estimating concentration of an analyte in a non-invasive manner, and an apparatus and method for generating a model for estimating concentration of an analyte in a non-invasive manner.

In an example embodiment, there is provided an apparatus for estimating concentration, the apparatus including: a spectrum obtainer configured to obtain Raman spectra of an object; and a processor configured to extract, from the Raman spectra, at least one analyte spectrum related to an analyte and at least one non-analyte spectrum related to a biological component other than the analyte, and estimate concentration of the analyte based on a first area under a curve of the at least one analyte spectrum and a second area under a curve of the at least one non-analyte spectrum.

The spectrum obtainer may be further configured to receive the Raman spectra from an external device, or measure the Raman spectra by emitting light onto the object and receiving Raman-scattered light returning from the object.

The analyte may be any one of glucose, triglyceride, urea, uric acid, lactate, protein, cholesterol, or ethanol.

The processor may include: a spectrum extractor configured to extract the at least one analyte spectrum and the at least one non-analyte spectrum from the Raman spectra; a background signal remover configured to remove a background signal from the at least one analyte spectrum and the at least one non-analyte spectrum; an area calculator configured to calculate the first area under the curve the at least one analyte spectrum, from which the background signal is removed, and calculate the second area under the curve of the at least one non-analyte spectrum, from which the background signal is removed; and a concentration estimator configured to estimate the concentration of the analyte based on the first area and the second area.

The spectrum extractor may be further configured to extract a spectrum of a Raman band related to the analyte as the at least one analyte spectrum, and extract a spectrum of a Raman band related to the biological component other than the analyte as the at least one non-analyte spectrum.

The analyte may be glucose; and the spectrum extractor may be further configured to extract at least one of Raman band spectra at 911 $cm^{-1}$, 1060 $cm^{-1}$, and 1125 $cm^{-1}$ as the at least one analyte spectrum, and extract at least one of Raman band spectra at 1003 $cm^{-1}$ and 1450 $cm^{-1}$ as the at least one non-analyte spectrum.

The background signal remover may be further configured to generate a background line by connecting a starting point and an ending point of each of the at least one analyte spectrum and the at least one non-analyte spectrum in a straight line or a curved line, and remove the background signal by subtracting the generated background line from each of the at least one analyte spectrum and the at least one non-analyte spectrum.

The concentration estimator may be further configured to estimate the concentration of the analyte based on the first area of the at least one analyte spectrum, from which the background signal is removed, the second area of the at least one non-analyte spectrum, from which the background signal is removed, and a concentration estimation model.

The concentration estimation model may define a relationship between the first area of the at least one analyte spectrum, from which the background signal is removed, the second area of the at least one non-analyte spectrum, from which the background signal is removed, and the concentration of the analyte.

The concentration estimation model may be generated by regression analysis or machine learning using a first reference area under a curve of a reference analyte spectrum, from which a background signal of the reference analyte spectrum is removed, a second reference area under a curve of a reference non-analyte spectrum, from which a background signal of the reference non-analyte spectrum is removed, and a corresponding concentration of the analyte.

The processor may further include a preprocessor configured to remove noise from the Raman spectra.

In another example embodiment, there is provided an apparatus for generating a concentration estimation model, the apparatus including: a learning data collector configured to collect, as learning data, Raman spectra of an object and concentration information of an analyte corresponding to the Raman spectra; and a processor configured to extract at least one analyte spectrum related to the analyte and at least one non-analyte spectrum related to a biological component other than the analyte from the Raman spectra, and generate the concentration estimation model based on a first area under a curve of the at least one analyte spectrum, a second area under a curve of the at least one non-analyte spectrum, and the concentration information of the analyte.

The processor may include: a spectrum extractor configured to extract the at least one analyte spectrum and the at least one non-analyte spectrum from the Raman spectra; a background signal remover configured to remove a background signal from the at least one analyte spectrum and the at least one non-analyte spectrum; an area calculator configured to calculate the first area under the of the at least one analyte spectrum, from which the background signal is removed, and the second area under the curve of the at least one non-analyte spectrum from which the background signal is removed; and a model generator configured to generate the concentration estimation model by using the first area, the second area, and the concentration information as training data.

The analyte may be glucose; and the spectrum extractor may be further configured to extract at least one of Raman band spectra at 911 $cm^{-1}$, 1060 $cm^{-1}$, and 1125 $cm^{-1}$ as the at least one analyte spectrum, and extract at least one of Raman band spectra at 1003 $cm^{-1}$ and 1450 $cm^{-1}$ as the at least one non-analyte spectrum.

The background signal remover may be further configured to generate a background line by connecting a starting point and an ending point of each of the at least one analyte spectrum and the at least one non-analyte spectrum in a straight line or a curved line, and remove the background signal by subtracting the background line from each of the at least one analyte spectrum and the at least one non-analyte spectrum.

The apparatus of claim 13, wherein the processor may further include a concentration estimator configured to generate the concentration estimation model by regression analysis or machine learning using the first area of the at least one analyte spectrum, from which the background signal is removed, the first area of the at least one non-analyte spectrum, from which the background signal is removed, and the concentration information of the analyte.

In another example embodiment, there is provided a method for estimating concentration, the method including: obtaining Raman spectra of an object; extracting, from the Raman spectra, at least one analyte spectrum related to an analyte and at least one non-analyte spectrum related to a biological component other than the analyte; removing a background signal from the at least one analyte spectrum and the at least one non-analyte spectrum; calculating a first area under a curve the at least one analyte spectrum, from which the background signal is removed, and a second area under a curve of the at least one non-analyte spectrum from which the background signal is removed; and estimating a concentration of the analyte based on the first area and the second area.

The obtaining the Raman spectra may include obtaining the Raman spectra by receiving the Raman spectra from an external device, or by measuring the Raman spectra by emitting light onto the object and receiving Raman-scattered light returning from the object.

The analyte may be any one of glucose, triglyceride, urea, uric acid, lactate, protein, cholesterol, or ethanol.

The extracting the at least one analyte spectrum and the at least one non-analyte spectrum may include extracting a spectrum of a Raman band related to the analyte as the at least one analyte spectrum, and extracting a spectrum of a Raman band related to the biological component other than the analyte as the at least one non-analyte spectrum.

The analyte may be glucose; and the extracting the at least one analyte spectrum and the at least one non-analyte spectrum may include extracting at least one of Raman band spectra at 911 $cm^{-1}$, 1060 $cm^{-1}$, and 1125 $cm^{-1}$ as the at least one analyte spectrum, and extracting at least one of Raman band spectra at 1003 $cm^{-1}$ and 1450 $cm^{-1}$ as the at least one non-analyte spectrum.

The removing the background signal may include generating a background line by connecting a starting point and an ending point of each of the at least one analyte spectrum and the at least one non-analyte spectrum in a straight line or a curved line, and removing the background signal by subtracting the background line from each of the at least one analyte spectrum and the at least one non-analyte spectrum.

The estimating the concentration of the analyte may include estimating the concentration of the analyte based on the first area of the at least one analyte spectrum, from which the background signal is removed, the second area of the at least one non-analyte spectrum, from which the background signal is removed, and a concentration estimation model.

The concentration estimation model may be generated by regression analysis or machine learning using a first reference area under a curve of a reference analyte spectrum, from which a background signal of the reference analyte spectrum is removed, a second area under a curve of a reference non-analyte spectrum, from which a background signal of the reference non-analyte spectrum is removed, and a corresponding concentration of the analyte.

The method may further include removing noise from the Raman spectra.

BRIEF DESCRIPTION OF THE DRAWINGS

The above and/or other aspects will be more apparent by describing certain example embodiments, with reference to the accompanying drawings, in which.

Figure 1:
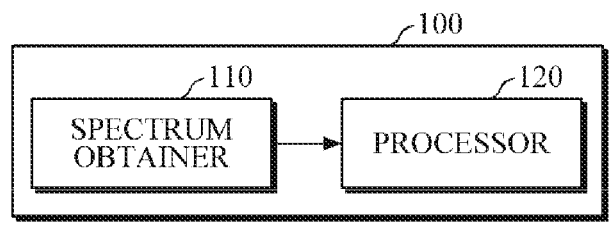
FIG. 1 is a block diagram illustrating an example of an apparatus for estimating concentration of an analyte.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

Figure 2:
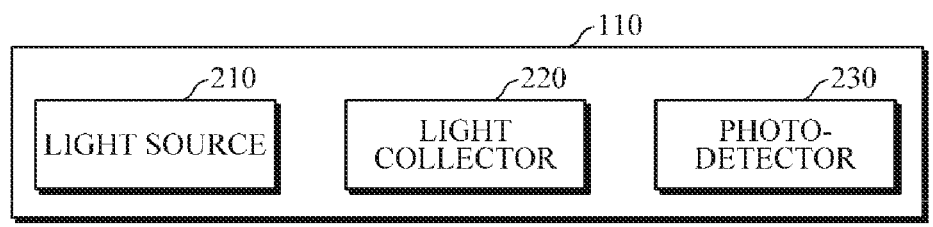
FIG. 2 is a block diagram illustrating an example of a spectrum obtainer.

FIG. 1 is a block diagram illustrating an example of an apparatus for estimating concentration of an analyte; and FIG. 2 is a block diagram illustrating an example of a spectrum obtainer. The apparatus 100 for estimating concentration of an analyte may non-invasively estimate the concentration of an analyte in an object by analyzing Raman spectra of the object, and may be embedded in an electronic device. Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 1, the apparatus 100 for estimating concentration of an analyte includes a spectrum obtainer 110 and a processor 120.

The spectrum obtainer 110 may obtain Raman spectra of an object.

In one example embodiment, the spectrum obtainer 110 may receive Raman spectra from an external device which measures and/or stores Raman spectra of an object. In this case, the spectrum obtainer 110 may use various communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like.

In another example embodiment, the spectrum obtainer 110 may be implemented as a spectrometer that emits light onto an object, and measures a Raman spectrum by receiving Raman-scattered light returning from the object. To this end, the spectrum obtainer 110 may include a light source 210, a light collector 220, and a photodetector 230, as illustrated in FIG. 2.

The light source 210 may emit light onto an object. For example, the light source 210 may emit light of a specific wavelength, e.g., near infrared rays (NIR) or mid infrared rays (MIR). However, wavelengths of light emitted by the light source 210 may vary according to a purpose of measurement or the types of component to be measured. Further, the light source 210 is not necessarily a single light emitting body, and may be formed as an array of a plurality of light emitting bodies. In the case where the light source 210 is configured as an array of a plurality of light emitting bodies, the plurality of light emitting bodies may emit light of different wavelengths according to the purpose of measurement, or all the light emitting bodies may emit light of the same wavelength. In one example embodiment, the light source 210 may include a light emitting diode (LED), a laser diode, and the like. However, this is merely exemplary, and the light source is not limited thereto.

In one example embodiment, the light source 210 may further include a filter (e.g., long pass filter, clean-up filter, band-pass filter, etc.) for selecting light of a specific wavelength, and/or an optical element (e.g., reflection mirror, etc.) for directing the light emitted by the light source 210 toward a desired position of an object.

The light collector 220 may collect Raman-scattered light from an object. To this end, the light collector 220 may include a filter (e.g., long pass filter, clean-up filter, etc.), a lens (e.g., collimating lens, focusing lens, etc.), a fiber, a waveguide, a grating, and the like.

The photodetector 230 may measure Raman spectra by receiving the Raman-scattered light collected by the light collector 220. In one example embodiment, the photodetector 230 may include a photo diode, a photo transistor (PTr), a charge-coupled device (CCD), and the like. The photodetector 230 is not necessarily a single device, and may be formed as an array of a plurality of devices.

The processor 120 may process various signals and operations for estimating concentration of an analyte. At predetermined intervals or at the request of a user, the processor 120 may control the spectrum obtainer 110 to obtain Raman spectra of an object, and may estimate the concentration of an analyte by analyzing the obtained Raman spectra.

Once the Raman spectra of the object is obtained, the processor 120 may extract at least one Raman band spectrum related to an analyte (hereinafter referred to as analyte spectrum), and at least one Raman band spectrum related to a biological component other than the analyte (hereinafter referred to as non-analyte spectrum), from among the obtained Raman spectra, and may estimate concentration of the analyte based on areas under the curve of the extracted analyte spectrum and non-analyte spectrum. Examples of the analyte may include glucose, triglyceride, urea, uric acid, lactate, protein, cholesterol, ethanol, and the like, but the analyte is not limited thereto. In the case where the analyte is glucose, the concentration of the analyte may indicate a blood glucose level.

Figure 3:
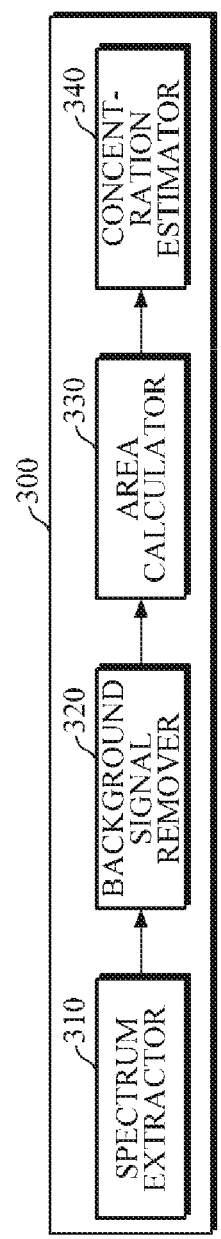
FIG. 3 is a block diagram illustrating an example of a processor.

FIG. 3 is a block diagram illustrating an example of a processor. The processor 300 of FIG. 3 may be an example of the processor 120 of FIG. 1.

Referring to FIG. 3, the processor 300 includes a spectrum extractor 310, a background signal remover 320, an area calculator 330, and a concentration estimator 340.

The spectrum extractor 310 may extract at least one analyte spectrum and at least one non-analyte spectrum from a Raman spectrum of an object. For example, the spectrum extractor 310 may extract a spectrum of a Raman band related to an analyte as an analyte spectrum, and may extract a spectrum of a Raman band related to a biological component other than the analyte as a non-analyte spectrum. In particular, information on the Raman band related to an analyte and information on the Raman band related to biological components other than the analyte may be obtained experimentally in advance and may be stored in an internal or external database.

For example, in the Raman spectrum, glucose is related to Raman bands at 911 cm$^{-1}$, a 1060 cm$^{-1}$, 1125 cm$^{-1}$ and the like; phenylalanine is related to a Raman band at 1003 cm$^{-1}$ and the like; proteins and lipid are related to a Raman band at 1450 cm$^{-1}$ and the like. Accordingly, in the case where the analyte is glucose, the spectrum extractor 310 may extract, as an analyte spectrum, at least one of Raman bands at 911 cm$^{-1}$, 1060 cm$^{-1}$, and 1125 cm$^{-1}$; and may extract, as a non-analyte spectrum, at least one of Raman bands at 1003 cm$^{-1}$ and 1450 cm$^{-1}$. In this case, the Raman band may indicate an interval where a peak of a corresponding wave number is formed, and the Raman band spectrum may indicate a spectrum of the corresponding interval. For example, in the case where a peak of a 911 cm$^{-1}$ Raman band is formed over a range of 910 cm$^{-1}$ to 925 cm$^{-1}$, the 911 cm$^{-1}$ Raman band may be in a range of 910 cm$^{-1}$ to 925 cm$^{-1}$, and the Raman band spectrum at 911 cm$^{-1}$ may be a spectrum in an interval of 910 cm$^{-1}$ to 925 cm$^{-1}$.

The background signal remover 320 may remove a background signal, such as fluorescence and the like, from the extracted at least one analyte spectrum and at least one non-analyte spectrum. In one example embodiment, the background signal remover 320 may generate a background line by connecting a starting point and an ending point of each of the extracted spectra (analyte spectrum and non-analyte spectrum) in a straight line or a curved line, and may remove a background signal by subtracting the generated background line from each spectrum. For example, when an analyte spectrum having a peak value at 911 cm$^{-1}$ is extracted, the starting point and the ending point of the analyte spectrum may be set to 910 cm$^{-1}$ and 925 cm$^{-1}$, respectively, and the value of a straight or curved line connecting the 910 cm$^{-1}$ and 925 cm$^{-1}$ may be removed from the analyte spectrum.

The area calculator 330 may calculate an area under the curve of each spectrum (analyte spectrum and non-analyte spectrum) from which the background signal is removed. For example, the area calculator 330 may calculate an area under the curve of each spectrum by performing integration of each spectrum (analyte spectrum and non-analyte spectrum) from which the background signal is removed.

The concentration estimator 340 may estimate concentration of an analyte based on the calculated area under the curve of each spectrum (analyte spectrum and non-analyte spectrum). For example, the concentration estimator 340 may estimate concentration of an analyte of an object based on the area under the curve of the analyte spectrum, from which the background signal is removed, the area under the curve of the non-analyte spectrum, from which the background signal is removed, and a concentration estimation model. In this case, the concentration estimation model defines a relationship between the area of the analyte spectrum, from which the background signal is removed, the area under the curve of the non-analyte spectrum, from which the background signal is removed, and the concentration of the analyte at this point in time. The concentration estimation model may be stored in an internal or external database. In one example embodiment, the concentration estimation model may be generated by regression analysis or machine learning using the areas under the curve of the analyte spectrum, from which the background signal is removed, the area under the curve of the non-analyte spectrum, from which the background signal is removed, and the corresponding concentration of the analyte. In this case, examples of a regression analysis algorithm may include linear regression (e.g., Partial least squares regression), logistic regression, proportional Cox regression, and the like; and examples of a machine learning algorithm may include Artificial Neural Network, Decision Tree, Genetic Algorithm, Genetic Programming, K-Nearest Neighbor, Radial Basis Function Network, Random Forest, Support Vector Machine, deep-learning, and the like.

In one example embodiment, the concentration estimation model may be represented by the following Equation 1 or Equation 2.

$$G = a_1 x_1 + \ldots + a_n x_n + b_1 y_1 + \ldots + b_m y_m + a_0 \quad \text{[Equation 1]}$$

$$G = \frac{1}{k}(a_1x_1 + \ldots + a_nx_n + b_1y_1 + \ldots + b_my_m + a_0) \quad \text{[Equation 2]}$$

Herein, G denotes the concentration of the analyte, denotes $x_i$ (i=1, ... n) the area under the curve of the analyte spectrum, from which the background signal is removed, $y_j$ (j=1, ... m) denotes the area under the curve of the non-analyte spectrum, from which the background signal is removed, $a_0$, $a_i$ (i=1, ... n), and $b_j$ (j=1, ... m) denote coefficients, and k denotes a normalization coefficient. In this case, $a_0$, $a_i$ (i=1, ... n), and $b_j$ (j=1, ... m) may be calculated using the regression analysis algorithm. Further, k may be a predetermined value, either $x_i$ (i=1, ... n) or $y_j$ (j=1, ... m).

Figure 4:
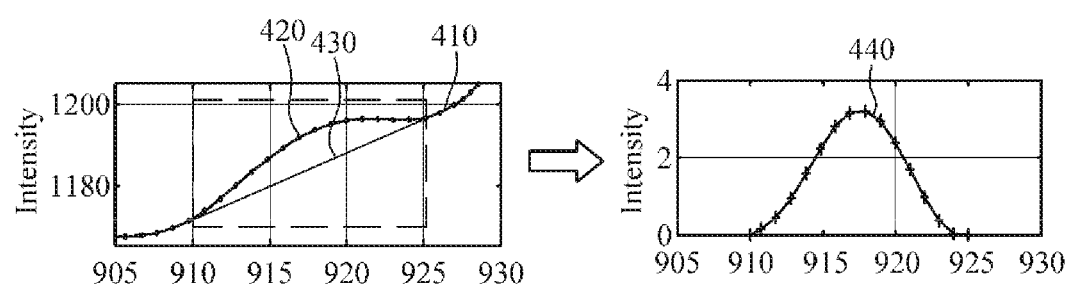
FIG. 4 is a diagram explaining an example of a method of extracting a spectrum and removing a background signal.

FIG. 4 is a diagram explaining an example of a method of extracting a spectrum and removing a background signal. FIG. 4 illustrates an example of extracting a spectrum of a Raman band related to glucose, and removing a background signal from the extracted Raman band spectrum.

In an example embodiment, the spectrum extractor 310 may determine a range of wave numbers for calculating an area under a curve (AUC) of the Raman spectrum 410, according to a target Raman band (e.g., a glucose-related Raman band of 911 $cm^{-1}$). In particular, the processor 300 may remove a background signal from the Raman spectrum 410, generate a first derivative signal from the background-signal-removed Raman spectrum 410, and determine a range between two adjacent zero or near-zero value positions (e.g., a range between 910 $cm^{-1}$ and 925 $cm^{-1}$) of the first derivative signal that includes the target Raman band (e.g., 911 $cm^{-1}$). For example, the range between two adjacent zero or near-zero value positions may correspond to a range between a first position where the first derivative signal changes from a positive value to a negative value (or from a negative value to a positive value) and a second point where the first derivative signal changes from a negative value to a positive value (or from a positive value to a negative value).

Referring to FIGS. 3 and 4, upon analyzing a Raman spectrum 410 of an object, the spectrum extractor 310 may determine that a peak at 911 $cm^{-1}$ is formed over a range of 910 $cm^{-1}$ to 925 $cm^{-1}$, and may extract a spectrum 420 over a range of 910 $cm^{-1}$ to 925 $cm^{-1}$ as a Raman band spectrum related to glucose. In this case, the spectrum 420 of 910 $cm^{-1}$ to 925 $cm^{-1}$ may be wave numbers, at which a primary differential value of a Raman spectrum, obtained by removing a background signal, such as fluorescence and the like, from the Raman spectrum 410, starts to change from a negative number to a positive number. The range of the spectrum 420 (e.g., the range of 910 $cm^{-1}$ to 925 $cm^{-1}$) may be calculated by the processor 300 based on a target peak wavenumber (e.g., 911 $cm^{-1}$), or may be pre-stored in the apparatus 100 as a predetermined value.

The background signal remover 320 may generate a baseline 430 by connecting a starting point and an ending point of the extracted Raman band spectrum 420 in a straight line or a curved line, and may generate a Raman band spectrum 440, from which a background signal such as fluorescence and the like is removed, by subtracting the baseline 430 from the extracted Raman band spectrum 420.

Figure 5:
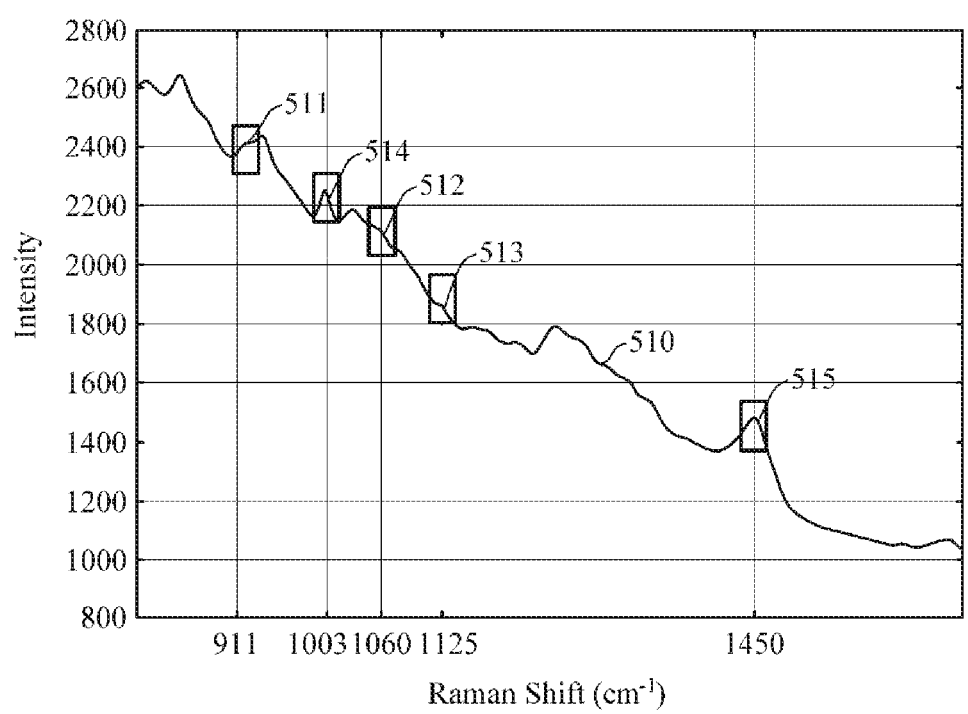
FIG. 5 is a diagram illustrating an example of a Raman spectrum of an object.
Figure 6:
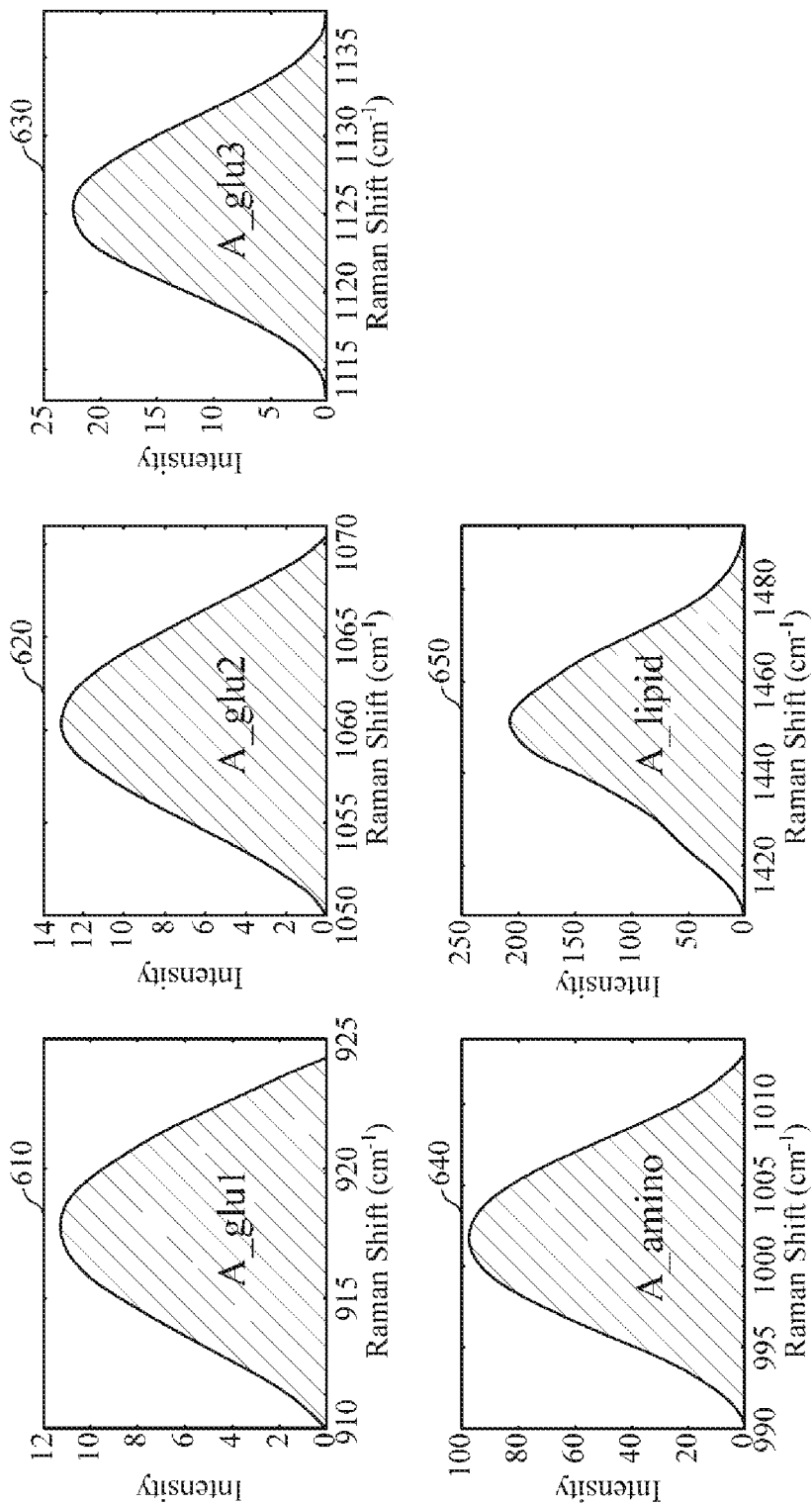
FIG. 6 is a diagram illustrating an example of an analyte spectrum and a non-analyte spectrum, from each of which a background signal is removed.

FIGS. 5 and 6 are exemplary diagrams explaining an example of a method of estimating concentration of an analyte. FIGS. 5 and 6 are diagrams illustrating an example where an analyte is glucose, and explaining a method of estimating blood glucose. More specifically, FIG. 5 is a diagram illustrating an example of a Raman spectrum of an object; and FIG. 6 is a diagram illustrating an example of an analyte spectrum and a non-analyte spectrum, from each of which a background signal is removed.

Referring to FIGS. 3, 5, and 6, the spectrum extractor 310 may extract, as analyte spectra, a Raman band spectrum 511 at 911 $cm^{-1}$, a Raman band spectrum 512 at 1060 $cm^{-1}$, and a Raman band spectrum 513 at 1125 $cm^{-1}$, which are related to glucose; and may extract, as non-analyte spectra, a Raman band spectrum 514 at 1003 $cm^{-1}$ related to phenylalanine and a Raman band spectrum 515 at 1450 $cm^{-1}$ which is related to proteins and lipid.

The background signal remover 320 may generate a background line by connecting a starting point and an ending point of each of the extracted Raman band spectra 511 to 515 in a straight line or a curved line, and may generate Raman band spectra 610 to 650, from which the background signal is removed, by subtracting the background line from each of the extracted Raman band spectra 511 to 515. In FIG. 6, the Raman band spectrum 610 corresponds to the 911 $cm^{-1}$ Raman band spectrum 511, the Raman band spectrum 620 corresponds to the 1060 $cm^{-1}$ Raman band spectrum 512, and the Raman band spectrum 630 corresponds to the 1125 $cm^{-1}$ Raman band spectrum 513, the Raman band spectrum 640 corresponds to the 1003 $cm^{-1}$ Raman band spectrum 514, and the Raman band spectrum 650 corresponds to the 1450 $cm^{-1}$ Raman band spectrum 515.

The area calculator 330 may calculate areas A_glu1, A_glu2, A_glu3, A_amino, and A_lipid under the curve of each of the Raman band spectra 610 to 650 by performing integration of each of the Raman band spectra 610 to 650, from which a background signal is removed. The concentration estimator 340 may estimate a blood glucose level of an object based on the calculated areas A_glu1, A_glu2, A_glu3, A_amino, and A_lipid and a concentration estimation model. For example, the concentration estimator 340 may estimate a blood glucose level of an object by using Equation 1 or Equation 2.

Figure 7:
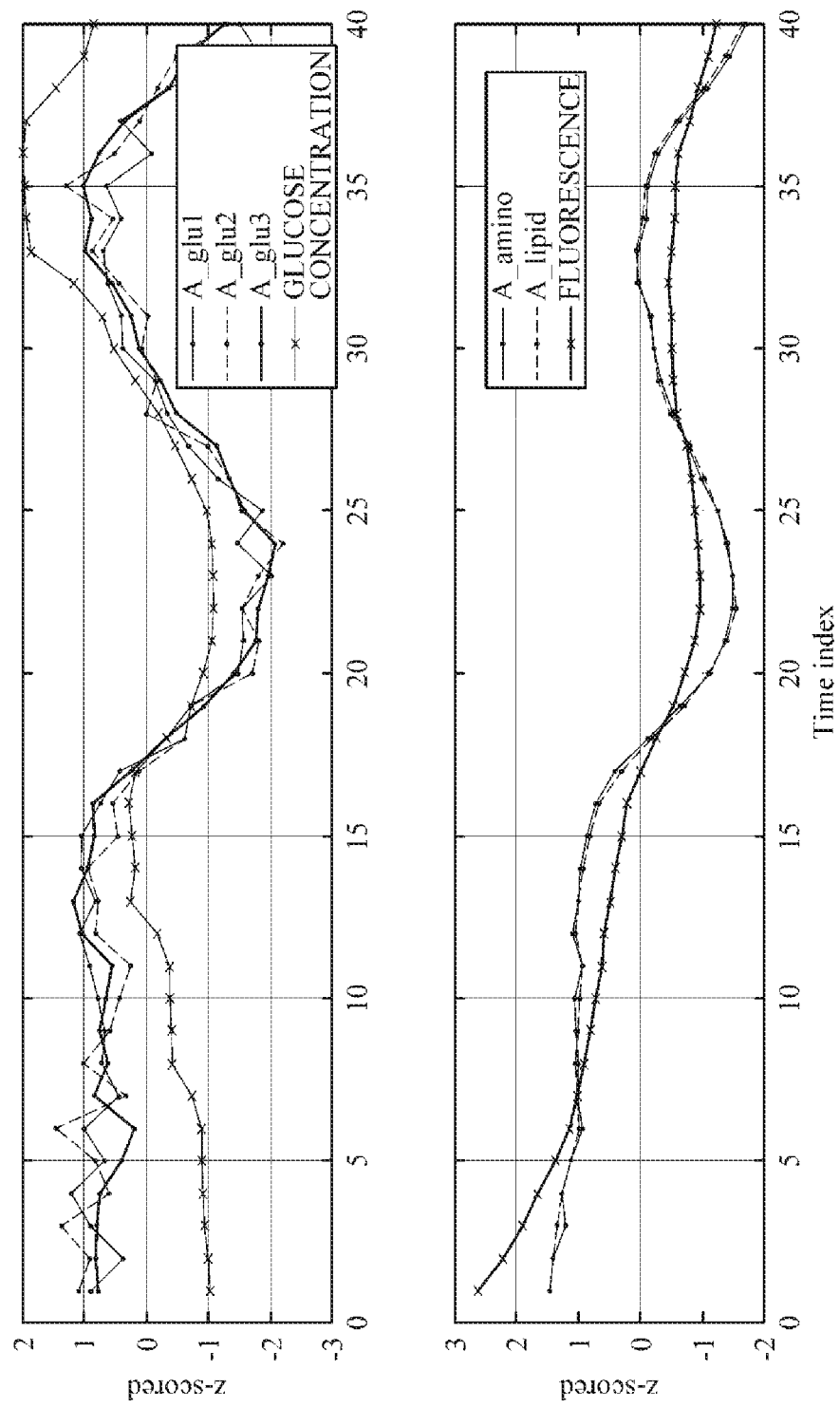
FIG. 7 is a diagram illustrating a relationship between an area of an analyte spectrum and blood glucose, and a relationship between an area of a non-analyte spectrum and a background signal.

FIG. 7 is a diagram illustrating a relationship between an area under the curve of an analyte spectrum and blood glucose, and a relationship between an area under the curve of a non-analyte spectrum and a background signal.

Referring to FIG. 7, a change in an area A_glu1 under the curve of a 911 $cm^{-1}$ Raman band spectrum, an area A_glu2 under the curve of a 1060 $cm^{-1}$ Raman band spectrum, and an area A_glu3 under the curve of a 1125 $cm^{-1}$ Raman band spectrum is similar to a change in glucose concentration. That is, it can be seen that the areas A_glu1, A_glu2, and A_glu3 of the analyte spectra are related to the glucose concentration.

Further, a change in an area A_amino under the curve of a 1003 $cm^{-1}$ Raman hand spectrum and an area A_lipid under the curve of a 1450 $cm^{-1}$ Raman band spectrum is similar to a change in a background signal, i.e., fluorescence. That is, each of the areas A_amino and A_lipid of the non-analyte spectra is related to the background signal.

Figure 8A:
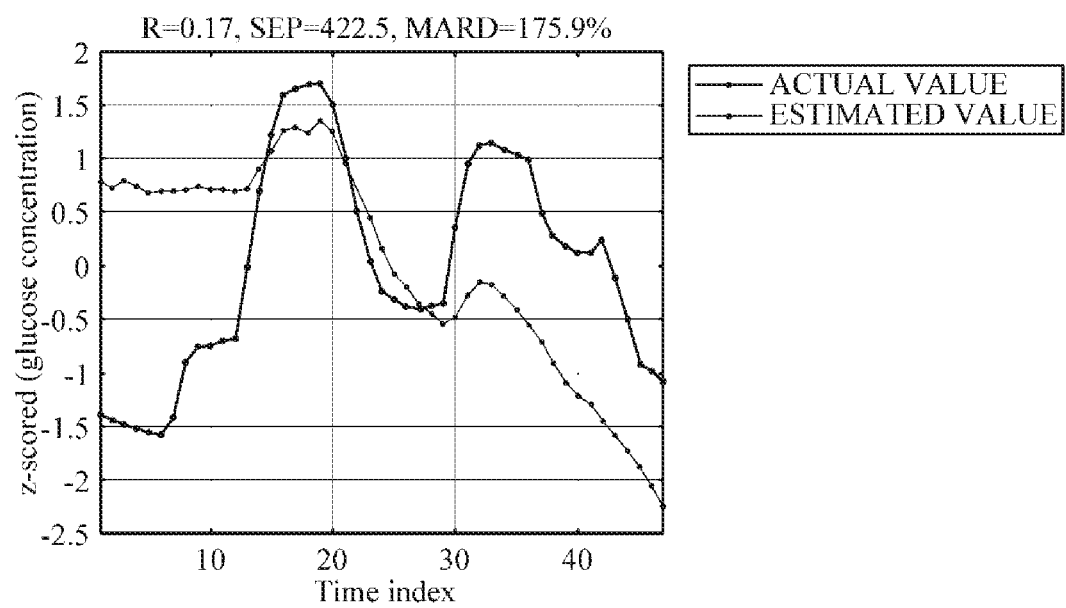
FIGS. 8A and 8B are diagrams illustrating an example of comparing an estimation result of blood glucose using general Raman spectroscopy analysis with an estimation result of blood glucose using a method of estimating concentration according to an example embodiment of the present disclosure.
Figure 8B:
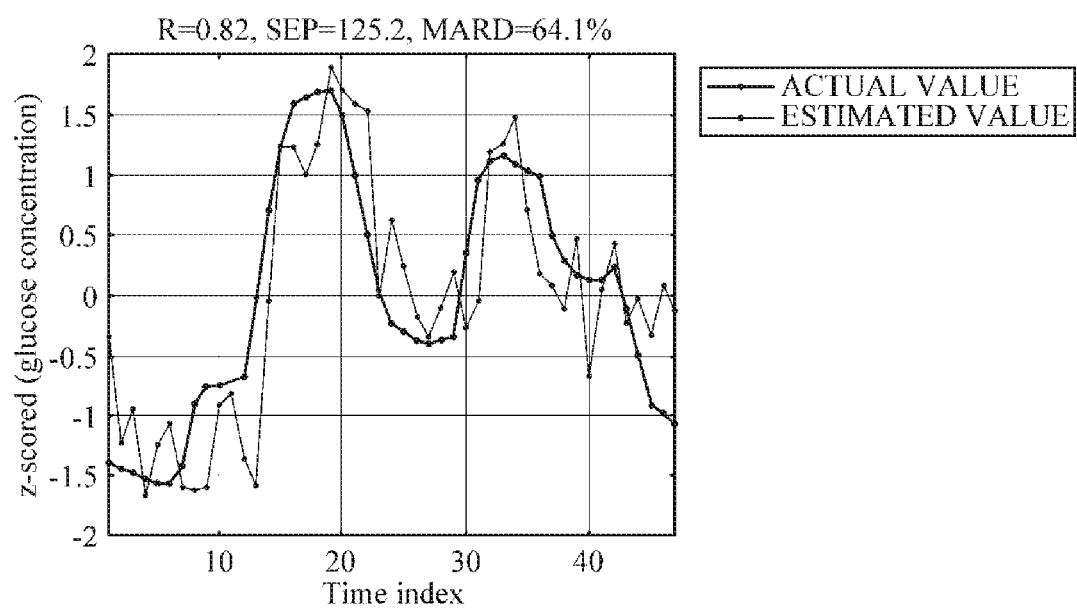

FIGS. 8A and 8B are diagrams illustrating an example of comparing an estimation result of blood glucose using general Raman spectroscopy analysis with an estimation result of blood glucose using a method of estimating concentration according to an example embodiment of the present disclosure. FIG. 8A illustrates a graph of an estimation result of blood glucose using general Raman spectroscopy analysis; and FIG. 8B illustrates a graph of an estimation result of blood glucose using a method of estimating concentration according to an example embodiment of the present disclosure.

As illustrated in FIG. 8A, in the case of estimating blood glucose using general Raman spectroscopy analysis, a correlation coefficient R is 0.17, a standard error of prediction (SEP) is 422.5 mg/dL, and a mean absolute relative difference (MARD) is 175.9%. By contrast, as illustrated in FIG. 8B, in the case of estimating blood glucose using a method of estimating concentration according to an example embodiment of the present disclosure, the R is 0.82, the SEP is 125.2 mg/dL, and the MARD is 64.1%. As the R increases and the SEP and the MARD decreases, accuracy of estimation increases. Accordingly, it can be seen that in the case of estimating blood glucose using the method of estimating concentration according to an example embodiment of the present disclosure (FIG. 8B), accuracy of estimation is improved in comparison with the case of estimating blood glucose using general Raman spectroscopy analysis (FIG. 8A).

Particularly, in an initial interval at the beginning of estimating blood glucose when there is a large change in fluorescence changes, accuracy of estimation is relatively low in the case where blood glucose is estimated using the general Raman spectroscopy method (FIG. 8A), but accuracy of estimation is maintained at a relatively high level in the case where blood glucose is estimated using the method of estimating concentration according to an example embodiment of the present disclosure (FIG. 8B).

Figure 9:
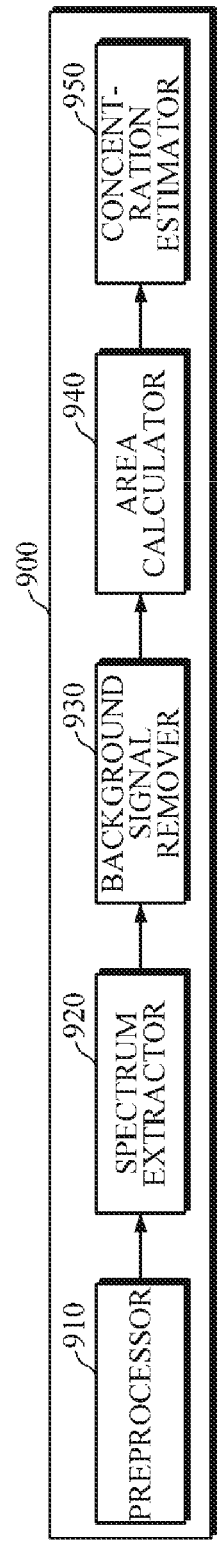
FIG. 9 is a block diagram illustrating another example of a processor.

FIG. 9 is a block diagram illustrating another example of a processor. The processor 900 of FIG. 9 may be an example of the processor 120 of FIG. 1.

Referring to FIG. 9, the processor 900 includes a preprocessor 910, a spectrum extractor 920, a background signal remover 930, an area calculator 940, and a concentration estimator 950. Here, the spectrum extractor 920, the background signal remover 930, the area calculator 940, and the concentration estimator 950 may operate in substantially the same manner as the spectrum extractor 310, the background signal remover 320, the area calculator 330, and the concentration estimator 340, such that detailed description thereof will be omitted.

The preprocessor 910 may remove noise from a Raman spectrum of an object. In one example embodiment, the preprocessor 910 may remove noise from the Raman spectrum of the object based on various noise removal algorithms such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like, but the noise removal algorithm is not limited thereto.

Figure 10:
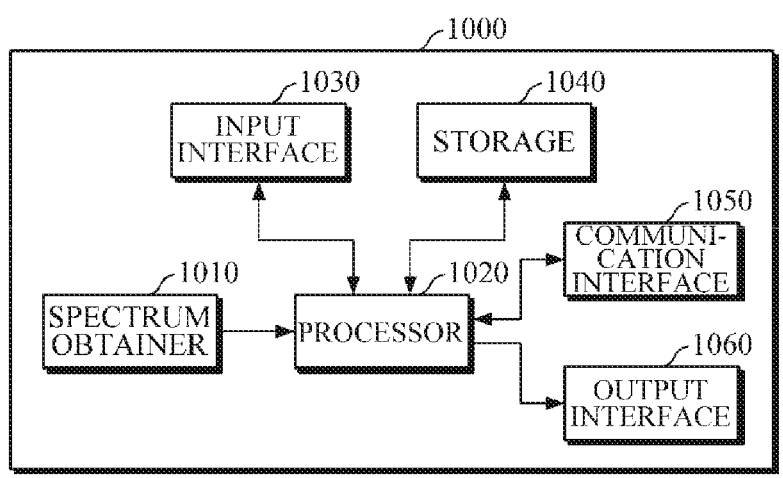
FIG. 10 is a block diagram illustrating another example of an apparatus for estimating concentration of an analyte.

FIG. 10 is a block diagram illustrating another example of an apparatus for estimating concentration of an analyte. The apparatus 1000 for estimating concentration is a non-invasive apparatus for estimating concentration of an analyte in an object, and may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 10, the apparatus 1000 for estimating concentration includes a spectrum obtainer 1010, a processor 1020, an input interface 1030, a storage 1040, a communication interface 1050, and an output interface 1060. Here, the spectrum obtainer 1010 and the processor 1020 are the same as the spectrum obtainer 110 and the processor 120 of FIG. 1, such that detailed description thereof will be omitted.

The input interface 1030 may receive input of various operation signals from a user. In one example embodiment, the input interface 1030 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 1040 may store programs or commands for operation of the apparatus 1000 for estimating concentration, and may store data input to and output from the apparatus 1000 for estimating concentration. Further, the storage 1040 may store a Raman spectrum, a concentration estimation model, an estimated concentration value of an analyte, and the like. The storage 1040 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 1000 for estimating concentration may operate an external storage medium, such as web storage and the like, which performs a storage function of the storage 1040 on the Internet.

The communication interface 1050 may perform communication with an external device. For example, the communication interface 1050 may transmit data input to and stored in the apparatus 1000 for estimating concentration, data processed by the apparatus 1000 for estimating concentration, and the like to the external device, or may receive, from the external device, various data useful for estimating concentration of an analyte.

In this case, the external device may be medical equipment using the data input to and stored in the apparatus 1000 for estimating concentration, the data processed by the apparatus 1000 for estimating concentration, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 1050 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 1060 may output the data input to and stored in the apparatus 1000 for estimating concentration, the data processed by the apparatus 1000 for estimating concentration, and the like. In one example embodiment, the output interface 1060 may output the data input to and stored in the apparatus 1000 for estimating concentration, the data processed by the apparatus 1000 for estimating concentration, and the like by using at least one of an acoustic method, a visual method, and a tactile method. To this end, the output interface 1060 may include a display, a speaker, a vibrator, and the like.

Figure 11:
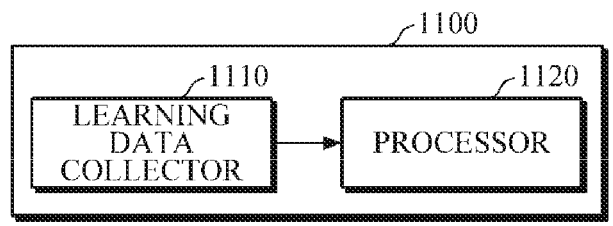
FIG. 11 is a block diagram illustrating an example of an apparatus for generating a concentration estimation model.

FIG. 11 is a block diagram illustrating an example of an apparatus for generating a concentration estimation model. The apparatus 1100 for generating a concentration estimation model of FIG. 11 may generate a model for estimating concentration of an analyte in an object, and may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto. The apparatus 1100 may be provided as part of the apparatus 1000 or separately provided from the apparatus 1000.

Referring to FIG. 11, the apparatus 1100 for generating a concentration estimation model includes a learning data collector 1110 and a processor 1120.

The learning data collector 1110 may collect, as learning data, a Raman spectrum of an object and concentration information of an analyte corresponding to the Raman spectrum. In particular, the Raman spectra collected as learning data may be a plurality of Raman spectra measured at predetermined time intervals during a predetermined period of time, and may be a representative Raman spectrum extracted from among the plurality of Raman spectra. Further, the Raman spectra collected as learning data may be raw data, from which noise is not removed, or may be data, from which noise is removed.

Once the Raman spectra of an object are collected, the processor 1120 may extract at least one analyte spectrum and at least one non-analyte spectrum from the collected Raman spectra, and may generate a concentration estimation model by learning areas of the extracted analyte spectrum and non-analyte spectrum and corresponding concentration values of the analyte.

Figure 12:
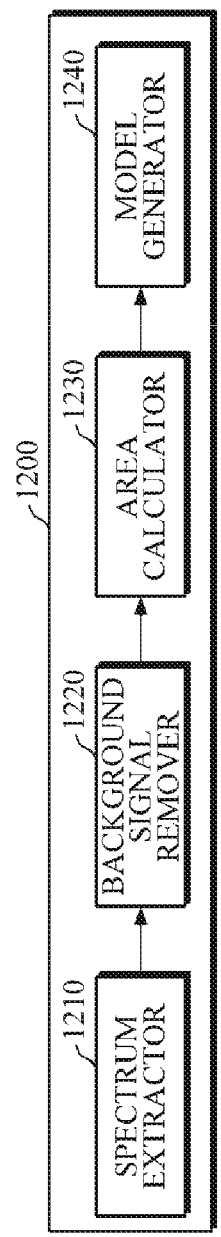
FIG. 12 is a block diagram illustrating an example of a processor.

FIG. 12 is a block diagram illustrating an example of a processor. The processor 1200 of FIG. 12 may be an example of the processor 1120 of FIG. 11.

Referring to FIG. 12, the processor 1200 includes a spectrum extractor 1210, a background signal remover 1220, an area calculator 1230, and a model generator 1240.

The spectrum extractor 1210 may extract at least one analyte spectrum and at least one non-analyte spectrum from Raman spectra of an object. For example, the spectrum extractor 1210 may extract a spectrum of a Raman band related to an analyte as an analyte spectrum and a spectrum of a Raman band related to a biological component other than the analyte as a non-analyte spectrum. In particular, information on the Raman band related to an analyte and the Raman band related to biological components other than the analyte may be obtained experimentally in advance and may be stored in an internal or external database.

The background signal remover 1220 may remove a background signal, such as fluorescence and the like, from the extracted at least one analyte spectrum and at least one non-analyte spectrum. In one example embodiment, the background signal remover 1220 may generate a background line by connecting a starting point and an ending point of each of the extracted spectra (analyte spectrum and non-analyte spectrum) in a straight line or a curved line, and may remove the background signal by subtracting the generated background line from each of the extracted spectra.

The area calculator 1230 may calculate an area under the curve of each spectrum (analyte spectrum and non-analyte spectrum), from which the background signal is removed. For example, the area calculator 1230 may calculate the area under the curve of each spectrum by performing integration of each spectrum (analyte spectrum and non-analyte spectrum), from which the background signal is removed.

The model generator 1240 may generate a concentration estimation model of an analyte based on the calculated area under the curve of each spectrum (analyte spectrum and non-analyte spectrum) and a corresponding concentration value of the analyte. For example, the model generator 1240 may generate the concentration estimation model by regression analysis or machine learning using the area under the curve of the analyte spectrum, from which the background signal is removed, the area under the curve of the non-analyte spectrum, from which the background signal is removed, and the corresponding concentration value of the analyte. Examples of a regression analysis algorithm may include linear regression (e.g., Partial least squares regression), logistic regression, proportional Cox regression, and the like; and examples of a machine learning algorithm may include Artificial Neural Network, Decision Tree, Genetic Algorithm, Genetic Programming, K-Nearest Neighbor, Radial Basis Function Network, Random Forest, Support Vector Machine, deep-learning, and the like.

For example, the concentration estimation model may be represented by the above Equation 1 or Equation 2.

Figure 13:
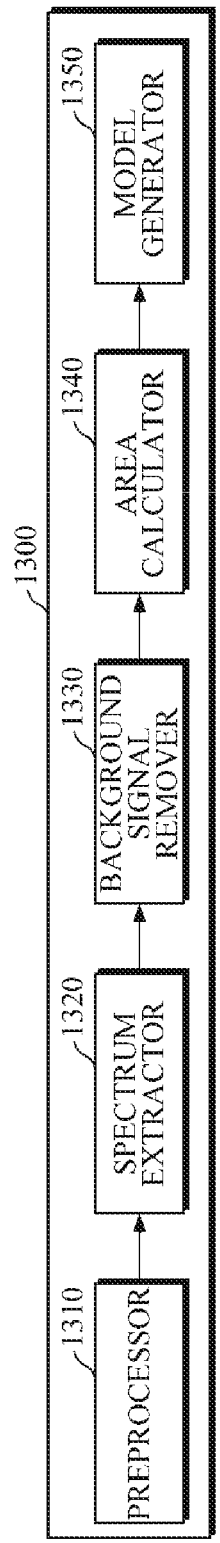
FIG. 13 is a block diagram illustrating another example of a processor.

FIG. 13 is a block diagram illustrating another example of a processor. The processor 1300 of FIG. 13 may be another example of the processor 1120 of FIG. 11.

Referring to FIG. 13, the processor 1300 includes a preprocessor 1310, a spectrum extractor 1320, a background signal remover 1330, an area calculator 1340, and a model generator 1350. Here, the spectrum extractor 1320, the background signal remover 1330, the area calculator 1340, and the model generator 1350 are the same as the spectrum extractor 1210, the background signal remover 1220, the area calculator 1230, and the model generator 1240 of FIG. 12, such that detailed description thereof will be omitted.

The preprocessor 1310 may remove noise from a Raman spectrum of an object. In one example embodiment, the preprocessor 1310 may remove noise from the Raman spectrum of the object by using various noise removal algorithms such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like, but the noise removal algorithm is not limited thereto.

Figure 14:
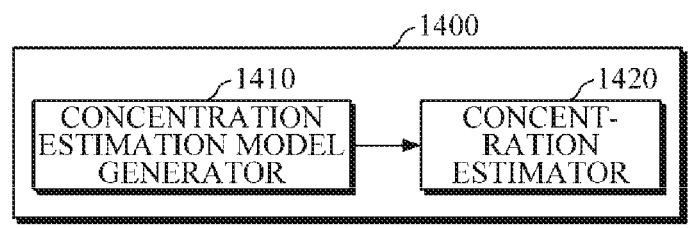
FIG. 14 is a block diagram illustrating another example of an apparatus for estimating concentration of an analyte.

FIG. 14 is a block diagram illustrating another example of an apparatus for estimating concentration of an analyte. FIG.

14 may be an example where the apparatus for generating a concentration estimation model and the apparatus for estimating concentration are implemented as a single apparatus.

As illustrated in FIG. 14, the apparatus 1400 for estimating concentration may include a concentration estimation model generator 1410 and a concentration estimator 1420. In particular, the concentration estimation model generator 1410 may correspond to the apparatus 1100 for generating a concentration estimation model described above with reference to FIGS. 11 to 13, and the concentration estimator 1420 may correspond to the apparatuses 100 and 1000 for estimating concentration described above with reference to FIGS. 1 to 10.

That is, the concentration estimation model generator 1410 may collect learning data during a predetermined period of time, and may generate a concentration estimation model of an analyte by learning the collected learning data. Once the concentration estimation model generator 1410 completes generating the concentration estimation model, the concentration estimator 1420 obtains a Raman spectrum of an object, and may estimate concentration of an analyte based on the obtained Raman spectrum and the generated concentration estimation model.

Figure 15:
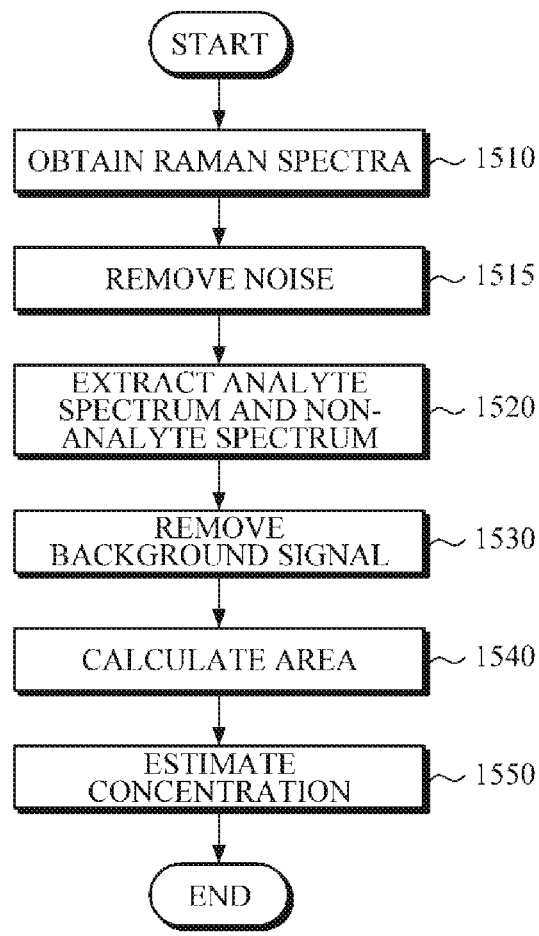
FIG. 15 is a flowchart illustrating an example of a method of estimating concentration of an analyte.

FIG. 15 is a flowchart illustrating an example of a method of estimating concentration of an analyte. The method of estimating concentration of an analyte of FIG. 15 may be performed by the apparatuses 100 and 1000 for estimating concentration of FIGS. 1 and 10.

Referring to FIG. 15, the apparatus for estimating concentration may obtain Raman spectra of an object in operation 1510. For example, the apparatus for estimating concentration may receive the Raman spectrum of the object from an external device which measures and/or stores Raman spectra of an object, or may measure the Raman spectrum of the object by emitting light onto an object and receiving Raman-scattered light returning from the object.

The apparatus for estimating concentration may remove noise from the obtained Raman spectra of the object in operation 1515. In one example embodiment, the apparatus for estimating concentration may remove noise from the Raman spectrum of the object based on various noise removal algorithms such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like, but the noise removal algorithm is not limited thereto.

The apparatus for estimating concentration may extract at least one analyte spectrum and at least one non-analyte spectrum from the Raman spectra of the object in operation 1520. For example, the apparatus for estimating concentration may extract a spectrum of a Raman band related to an analyte as an analyte spectrum and a spectrum of a Raman band related to a biological component other than the analyte as a non-analyte spectrum. In this case, information on the Raman band related to an analyte and the Raman band related to biological components other than the analyte may be obtained experimentally in advance and may be stored in an internal or external database.

The apparatus for estimating concentration may remove a background signal, such as fluorescence and the like, from the extracted at least one analyte spectrum and at least one non-analyte spectrum in operation 1530. For example, the apparatus for estimating concentration may generate a background line by connecting a starting point and an ending point of each of the extracted spectra (analyte spectrum and non-analyte spectrum) in a straight line or a curved line, and may remove the background signal by subtracting the generated background line from each of the extracted spectra.

The apparatus for estimating concentration may calculate an area under the curve of each spectrum (analyte spectrum and non-analyte spectrum), from which the background signal is removed, in operation 1540. For example, the apparatus for estimating concentration may calculate the area under the curve of each spectrum by performing integration of each spectrum (analyte spectrum and non-analyte spectrum), from which the background signal is removed.

The apparatus for estimating concentration may estimate concentration of an analyte based on the calculated area under the curve of each spectrum (analyte spectrum and non-analyte spectrum) in operation 1550. For example, the apparatus for estimating concentration may estimate concentration of an analyte of an object based on the area under the curve of the analyte spectrum, from which the background signal is removed, the area under the curve of the non-analyte spectrum, from which the background signal is removed, and a concentration estimation model. In one example embodiment, the concentration estimation model may be represented by the above Equation 1 or 2.

Figure 16:
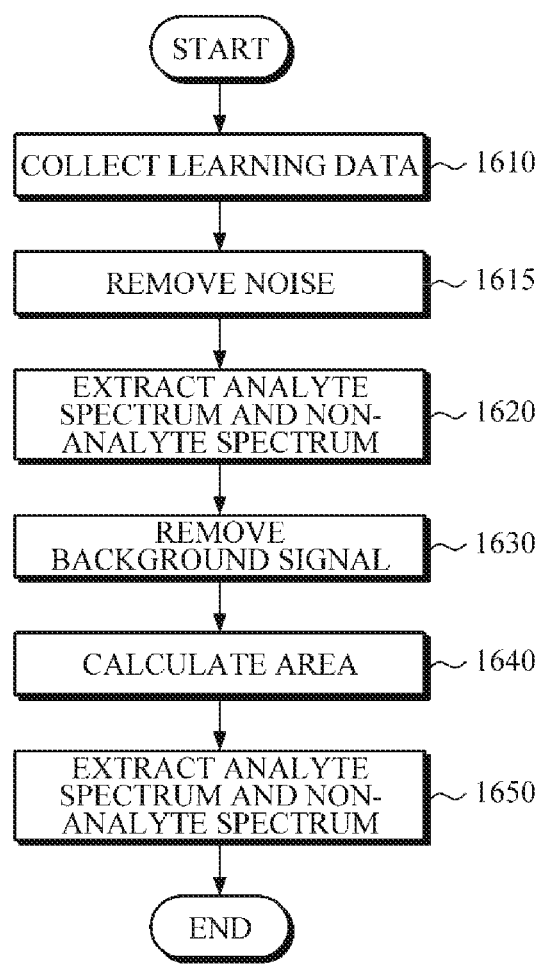
FIG. 16 is a flowchart illustrating an example of a method of generating a concentration estimation model.

FIG. 16 is a flowchart illustrating an example of a method of generating a concentration estimation model. The method of generating a concentration estimation model of FIG. 16 may be performed by the apparatus 1100 for generating a concentration estimation model of FIG. 11.

Referring to FIG. 16, the apparatus for generating a concentration estimation model may collect, as learning data, a Raman spectrum of an object and concentration information of an analyte corresponding to the Raman spectrum in operation 1610. In this case, the Raman spectra collected as learning data may be a plurality of Raman spectra measured at predetermined time intervals during a predetermined period of time, and may be a representative Raman spectrum extracted from among the Raman spectra.

The apparatus for generating a concentration estimation model may remove noise from the obtained Raman spectra of the object in operation 1615. In one example embodiment, the apparatus for estimating concentration may remove noise from the Raman spectra of the object based on various noise removal algorithms such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like, but the noise removal algorithm is not limited thereto.

The apparatus for generating a concentration estimation model may extract at least one analyte spectrum and at least one non-analyte spectrum from the Raman spectra of the object in operation 1620. For example, the apparatus for generating a concentration estimation model may extract a spectrum of a Raman band related to an analyte as an analyte spectrum and a spectrum of a Raman band related to a biological component other than the analyte as a non-analyte spectrum. In this case, information on the Raman band related to an analyte and information on the Raman band related to biological components other than the analyte may be obtained experimentally in advance and may be stored in an internal or external database.

The apparatus for generating a concentration estimation model may remove a background signal, such as fluorescence and the like, from the extracted at least one analyte spectrum and at least one non-analyte spectrum in operation 1630. For example, the apparatus for generating a concentration estimation model may generate a background line by connecting a starting point and an ending point of each of the extracted spectra (analyte spectrum and non-analyte spectrum) in a straight line or a curved line, and may remove the background signal by subtracting the generated background line from each of the extracted spectra.

The apparatus for generating a concentration estimation model may calculate an area under the curve of each spectrum (analyte spectrum and non-analyte spectrum), from which the background signal is removed, in operation 1640. For example, the apparatus for generating a concentration estimation model may calculate the area under the curve of each spectrum by performing integration of each spectrum (analyte spectrum and non-analyte spectrum), from which the background signal is removed.

The apparatus for generating a concentration estimation model may generate a concentration estimation model of an analyte based on the calculated area under the curve of each spectrum (analyte spectrum and non-analyte spectrum) and a corresponding concentration value of the analyte in operation 1650. For example, the apparatus for generating a concentration estimation model may generate the concentration estimation model by regression analysis or machine learning using the area under the curve of the analyte spectrum, from which the background signal is removed, the area under the curve of the non-analyte spectrum, from which the background signal is removed, and the corresponding concentration value of the analyte.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device for estimating concentration, the wearable device comprising:
    a spectrometer configured to obtain Raman spectra of an object;
    a memory storing a concentration estimation model that is generated by linear regression analysis using a first reference area under a curve of a reference glucose spectrum, a second reference area under a curve of a reference non-glucose spectrum, and a corresponding glucose level;
    a processor configured to:
        when the wearable device is worn by the object, extract, from the Raman spectra, at least one glucose spectrum related to glucose, and at least one non-glucose spectrum related to a biological component other than glucose, and
        estimate concentration of the glucose by retrieving the concentration estimation model from the memory and applying a first area under a curve of the at least one glucose spectrum and a second area under a curve of the at least one non-glucose spectrum to the concentration estimation model; and
    a display configured to display information of the concentration of the glucose.

2. The wearable device of claim 1, wherein the spectrometer is further configured to receive the Raman spectra from an external device, or measure the Raman spectra by emitting light onto the object and receiving Raman-scattered light returning from the object.

3. The wearable device of claim 1, wherein the processor is further configured to:
    remove a background signal from the at least one glucose spectrum and the at least one non-glucose spectrum; and
    calculate the first area under the curve of the at least one glucose spectrum, from which the background signal is removed, and calculate the second area under the curve of the at least one non-glucose spectrum, from which the background signal is removed.

4. The wearable device of claim 3, wherein the processor is further configured to extract a spectrum of a Raman band related to the glucose as the at least one glucose spectrum, and extract a spectrum of a Raman band related to the biological component other than the glucose as the at least one non-glucose spectrum.

5. The wearable device of claim 3, wherein the processor is further configured to:
    extract at least one of Raman band spectra at 911 $cm^{-1}$, 1060 $cm^{-1}$, and 1125 $cm^{-1}$ as the at least one glucose spectrum, and
    extract at least one of Raman band spectra at 1003 $cm^{-1}$ and 1450 $cm^{-1}$ as the at least one non-glucose spectrum.

6. The wearable device of claim 3, wherein the processor is further configured to:
    generate a background line by connecting a starting point and an ending point of each of the at least one glucose spectrum and the at least one non-glucose spectrum in a straight line or a curved line, and
    remove the background signal by subtracting the generated background line from each of the at least one glucose spectrum and the at least one non-glucose spectrum.

7. The wearable device of claim 3, wherein the processor is further configured to estimate the concentration of the glucose based on the first area of the at least one glucose spectrum, from which the background signal is removed, the second area of the at least one non-glucose spectrum, from which the background signal is removed, and the concentration estimation model.

8. The wearable device of claim 7, wherein the concentration estimation model defines a relationship between the first area of the at least one glucose spectrum, from which the background signal is removed, the second area of the at least one non-glucose spectrum, from which the background signal is removed, and the concentration of the glucose.

9. The wearable device of claim 3, wherein the processor further comprises a preprocessor configured to remove noise from the Raman spectra.

10. A wearable device for generating a concentration estimation model, the wearable device comprising:
a spectrometer configured to obtain, as learning data, Raman spectra of an object and concentration information of glucose corresponding to the Raman spectra; and
a processor configured to:
when the wearable device is worn by the object, extract at least one glucose spectrum related to the glucose and at least one non-glucose spectrum related to a biological component other than the glucose from the Raman spectra,
generate the concentration estimation model by linear regression analysis based on a first area under a curve of the at least one glucose spectrum, a second area under a curve of the at least one non-glucose spectrum, and the concentration information of the glucose;
storing the concentration estimation model in a memory of the wearable device; and
in response to a user request for measuring a blood glucose level being received by the wearable device, loading the concentration estimation model from the memory to provide the concentration estimation model.

11. The wearable device of claim 10, wherein the processor is further configured to:
extract the at least one glucose spectrum and the at least one non-glucose spectrum from the Raman spectra;
remove a background signal from the at least one glucose spectrum and the at least one non-glucose spectrum;
calculate the first area under the of the at least one glucose spectrum, from which the background signal is removed, and the second area under the curve of the at least one non-glucose spectrum from which the background signal is removed; and
generate the concentration estimation model by using the first area, the second area, and the concentration information as training data.

12. The wearable device of claim 11, wherein the processor is further configured to:
extract at least one of Raman band spectra at 911 cm$^{-1}$, 1060 cm$^{-1}$, and 1125 cm$^{-1}$ as the at least one glucose spectrum, and
extract at least one of Raman band spectra at 1003 cm$^{-1}$ and 1450 cm$^{-1}$ as the at least one non-glucose spectrum.

13. The wearable device of claim 11, wherein the processor is further configured to:
generate a background line by connecting a starting point and an ending point of each of the at least one glucose spectrum and the at least one non-glucose spectrum in a straight line or a curved line, and
remove the background signal by subtracting the background line from each of the at least one glucose spectrum and the at least one non-glucose spectrum.

14. A method for estimating concentration via a wearable device, the method comprising:
obtaining Raman spectra of an object;
while the wearable device is worn by the object, extracting, from the Raman spectra, at least one glucose spectrum related to glucose and at least one non-glucose spectrum related to a biological component other than the glucose;
removing a background signal from the at least one glucose spectrum and the at least one non-glucose spectrum;
calculating a first area under a curve of the at least one glucose spectrum, from which the background signal is removed, and a second area under a curve of the at least one non-glucose spectrum from which the background signal is removed;
retrieving a concentration estimation model that is generated by linear regression analysis using a first reference area under a curve of a reference glucose spectrum, a second reference area under a curve of a reference non-glucose spectrum, and a corresponding concentration of the glucose;
estimating a concentration of the glucose by applying the first area and the second area to the concentration estimation model; and
displaying information of the concentration of the glucose on the wearable device.

15. The method of claim 14, wherein the obtaining the Raman spectra comprises obtaining the Raman spectra by receiving the Raman spectra from an external device, or by measuring the Raman spectra by emitting light onto the object and receiving Raman-scattered light returning from the object.

16. The method of claim 14, wherein the extracting the at least one glucose spectrum and the at least one non-glucose spectrum comprises extracting a spectrum of a Raman band related to the glucose as the at least one glucose spectrum, and extracting a spectrum of a Raman band related to the biological component other than the glucose as the at least one non-glucose spectrum.

17. The method of claim 14, wherein the extracting the at least one glucose spectrum and the at least one non-glucose spectrum comprises:
extracting at least one of Raman band spectra at 911 cm$^{-1}$, 1060 cm$^{-1}$, and 1125 cm$^{-1}$ as the at least one glucose spectrum, and
extracting at least one of Raman band spectra at 1003 cm$^{-1}$ and 1450 cm$^{-1}$ as the at least one non-glucose spectrum.

18. The method of claim 14, wherein the removing the background signal comprises:
generating a background line by connecting a starting point and an ending point of each of the at least one glucose spectrum and the at least one non-glucose spectrum in a straight line or a curved line, and
removing the background signal by subtracting the background line from each of the at least one glucose spectrum and the at least one non-glucose spectrum.

19. The method of claim 14, wherein the estimating the concentration of the glucose comprises estimating the concentration of the glucose based on the first area of the at least one glucose spectrum, from which the background signal is removed, the second area of the at least one non-glucose spectrum, from which the background signal is removed, and the concentration estimation model.

20. The method of claim 14, further comprising removing noise from the Raman spectra.

* * * * *